United States Patent [19]

Benoit

[11] Patent Number: 5,177,098
[45] Date of Patent: Jan. 5, 1993

[54] PESTICIDAL COMPOSITIONS
[75] Inventor: Marc Benoit, Roquevaire, France
[73] Assignee: Roussel Uclaf, Paris, France
[21] Appl. No.: 711,169
[22] Filed: Jun. 5, 1991

Related U.S. Application Data

[63] Continuation of Ser. No. 439,589, Nov. 20, 1989, abandoned.

[30] Foreign Application Priority Data

Nov. 23, 1988 [FR] France ............................... 88 15244

[51] Int. Cl.$^5$ ...................... A01N 43/50; A01N 53/00
[52] U.S. Cl. .................................... 514/399; 514/521; 514/531
[58] Field of Search ............................. 514/399, 531

[56] References Cited

U.S. PATENT DOCUMENTS 4,853,414  8/1989  Robson et al. ...................... 514/531

OTHER PUBLICATIONS

Warthing et al, The Pesticide Manual, 8th ed. pp. 690 and 691 (1987).

*Primary Examiner*—Allen J. Robinson
*Attorney, Agent, or Firm*—Bierman and Muserlian

[57] ABSTRACT

A pesticidal composition comprising at least one pyrethrinoid and a synergistically effective amount of at least one fungicide compound selected from the group consisting of azoles and morpholines, especially useful against insects and parasitic plant and animal acaridae.

6 Claims, No Drawings

PESTICIDAL COMPOSITIONS

PRIOR APPLICATION

This application is a continuation of U.S. patent application Ser. No. 439,589 filed Nov. 20, 1989, now abandoned.

STATE OF THE ART

Related literature include U.S. Pat. Nos. 4,256,754 and 4,194,001, European patent No. 0,001,809 and No. 0,235,584, French patent No. 2,299,808 and German patent No. 3,641,553.

OBJECTS OF THE INVENTION

It is an object of the invention to provide improved pesticidal compositions and an improved method of killing pests.

These and other objects and advantages of the invention will become obvious from the following detailed descripted.

THE INVENTION

The novel pesticidal compositions of the invention are comprised of at least one pyrethrinoid and a synergistically effective amount of at least one fungicide compound selected from the group consisting of azoles and morpholines, especially imidazoles and triazoles.

Examples of preferred pyrethrinoid compounds are deltamethrin, tralomethrin, nococythrin, fenpropathrin, fenvalerate, cyhalothrin, fluvalinate, permethrin, phenothrin, flucythrinate, cyfluthrin, bifenthrin, tefluthrin, fenfluthrin, or furthermore bioresmethrin, bioallethrin, prallethrin, tetramethrin, kadethrin, empenthrin, terrallethrin and flumethrin. Equally useful are the pyrethrinoids described in European patents No. 0,038,271; No. 0,041,021; No. 0,048,186; No. 0,050,534; No. 0,110,769; No. 0,114,012; No. 281,439 and the French patent No. 2,536,389.

Preferred are the compositions in which the fungicide is prochloraze or imazalil as well as those wherein the fungicide is flusilazol or diclobutrazole, triadimenol, propiconazole or fenpropimorph.

Prochloraze or N-propyl-N-[2-(2,4,6-trichlorophenoxy)-ethyl-imidazol-1-carboxamide is a product well known for its fungicide properties [cf on this subject: The Pesticide Manual 7th edition published by the British Crop Protection Council, p. 452]. Imazalil or allyl 1-(2,4-dichlorophenyl)-2-imidazol-1-yl-ethyl ether is a fungicide known for its systemic properties [see, The Pesticide Manual 7th edition published by The British Crop Protection Council, p. 315]. Flusilazol or 1-[[bis-4-fluoro-benzyl-silyl]-methyl]-1H-1,2,4-triazole is equally a known fungicide product [see The Agrochemicals Handbook 2nd edition]. Diciobutrazole or (2RS,3RS)-1-(2,4-dichlorophenyl)-4,4-dimethyl-2-(1H-1,2,4-triazol-1-yl)-pentane-3-ol is a fungicide well known for its diverse applications [see The Pesticide Manual, 7th edition published by The British Crop Protection Council, p. 186].

Triadimenol or 1-(4-chlorophenoxy)-3,3-dimethyl-1-(1H-1,2,4-triazol-1-yl)-butan-2-ol is equally well known for its fungicide properties (see The Agrochemicals Handbook 2nd edition). Propiconazole or ($\pm$)-1-[2-(2,4-dichlorophenyl)-4-propyl-1,3-dioxolan-2-yl-methyl]-1H-1,2,4-triazol (see on this subject The Pesticide Manual 7th edition published by The British Crop Protection Council, p. 468). Fenpropimorph or ($\pm$)-cis-4-[3-(4-tert-butylphenyl)-2-methylpropyl]-2,6-dimethylmorpholine is described in "The Pesticide Manual" 7th edition published by The British Crop Protection Council, p. 265.

Among the preferred compositions of the invention are the compositions wherein the pyrethrinoid is selected from the group consisting of deltamethrin, tralomethrin, nococythrin, fenpropathrin, fenvalerate, cyhalothrin, fluvalinate, permethrin, phenothrin, flucythrinate, cyfluthrin, bifenthrin, tefluthrin and fenfluthrin and especially the compositions containing deltamethrin or tefluthrin.

Among the preferred compositions of the invention are the compositions containing (S)-cyano-3 phenoxybenzyl (1R,cis)-2,2 dimethyl-3-[(Z)-3-oxo-3-(1,1,1,3,3,3-hexafluoro-isopropoxy)-1-propenyl]-cyclopropane-carboxylate (hereafter called product A), one of its stereoisomers and the diverse mixtures of possible stereoisomers (cf European patent No. 0,048,186) or pentafluorobenzyl 1R,cis-(E)-2,2-dimethyl-3-[3-oxo-3-methoxy-2-fluoro-1-propenyl]-cyclopropane carboxylate, one of its stereoisomers and the diverse mixtures of possible stereoisomers, (cf European patent No. 0,050,534 and French patent No. 2,536,389).

The presence of azoles and morpholines and especially imidazoles and triazoles such as prochloraze, imazalil, flusilazol, diclobutrazole, triadimenol, propiconazole or fenpropimorph increased in a very marked fashion the insecticide and acaricide activity of pyrethrinoids. The results of biological tests set out hereafter clearly shows the synergistic character of the compositions containing a pyrethrinoid, for example tefluthrine, deltamethrine or product A and prochloraze, imazazlil, flusilazol, dichlobutrazole, triadimenol, propiconazole or fenpropimorph. The results obtained are particularly interesting on Diabrotica and other soil parasites, equally good results are obtained on lepidopterea notably, on Spodoptera littoralis, on parasitic plant acaridae such as Tetranyques or also parasitic animal acaridae, for example ticks and notably ticks of the type Boophilus, Hyalomnia, Amblyomnia and Rhipicephalus and all sorts of mites, notably sarcoptic mites the psoroptic mites and chorioptic mites.

The presence of azoles and of morpholines also cause a consideable reduction in the resistance of insects to pyrethrinoids, notably the resistance of Spodotera littoralis to pyrethrinoids.

Therefore, a more particular subject of the invention is the pesticide compositions characterized in that they are intended for combating insects of the soil, or furthermore the compositions wherein they are intended for combating insects living off the leaves of plants, as for example, lepidoptera as well as compositions intended for combating parasitic plant or animal acaridae.

Preferred are compositions containing from 10 to 1,000 parts by weight of fungicide to 1 part by weight of pyrethrinoid, and especially compositions containing from 10 to 1,000 part by weight of prochloraze, imazalil, flusilazol, diclobutrazole, triadimenol, propiconazole or fenpropimorph to one part by weight of pyrethrinoid.

Among the preferred compositions are compositions containing 30 to 600 parts by weight of prochloraze, imazalil, flusilazol, diclobutrazole, triadimenol, propiconazole or fenpropimorph to one part by weight of pyrethrinoid as for example compositions containing 40 to 60 parts by weight of prochloraze, imazalil, flusilazol, diclobutrazole, triadimenol, propiconazole or fenpropimorph to one part by weight of deltamethrin or tefluthrin and especially those containing 400 to 600 parts by weight of prochloraze or flusilazol to 1 part by weight of deltamethrin or tefluthrin.

The compositions of the invention are prepared according to standard processes of the agro-chemical industry or the veterinary industry. In compositions intended for agricultural use and for household use, the active material(s) can optionally contain also one or more other pesticidal agents. The compositions can be in the form of powders, granules, suspensions, emulsions, solutions, aerosol solutions, baits or other preparations usually employed.

In addition to the active principle, the compositions generally contain a vehicle and/or a non-ionic surface-active agent to ensure a uniform dispersion of the constituent substances of the mixture. The vehicle can be a liquid such as water, alcohol, hydrocarbons or other organic solvents, a mineral, animal or vegetable oil or a powder such as talc, clays silcates, kieselghr or a combustible acid.

To enhance the biological activity of the compositions of the invention, they may contain standard synergists such as 1-(2,5,8-trioxadodecyl)-2-propyl-4,5-methylendioxy benzene (or piperonyl butoxide) or N-(2-ethyl heptyl)-bicyclo-[2,2-1]-5-heptene-2,3-dicarboximide, or piperonyl-bis-2(2'-n-butoxy ethoxy) ethylacetal (or tropital).

The novel method of the invention for combatting pests comprises contacting the pests with a pestically effective amount of a pesticidal composition comprising at least one pyrethrinoid and a synergistically effective amount of at least one fungicide compound selected from the group consisting of azoles and morpholines, especially imidazoles and triazoles.

In the following examples there are described several preferred embodiments to illustrate the invention. However, it is to be understood that the invention is not intended to be limited to the specific embodiments.

EXAMPLE 1

An emulsifiable concetrate was prepared containing 2 g of Telfuthrin, 500 g of Prochloraze, 95 g of Tween 80, 95 g of Topanol A and 95 g of Xylene.

EXAMPLE 2

An emulsifiable concentrate was prepared containing 1 g of deltamethrin, 50 g of prochloraze and 50 g of piperonyl butoxide.

EXAMPLE 3

An acetonic solution of 100 mg of tefluthrin and 50 g of prochloraze per liter of acetone (solution A) was prepared.

EXAMPLE 4

An acetonic solution was prepared containing 100 mg of tefluthrin per 5 g of prochloraze per liter (solution B).

EXAMPLE 5

An acetonic solution was prepared containing 100 mg of tefluthrin per 5 g of flusilazol per liter (solution C).

EXAMPLE 6

An acetonic solution was prepared containing one part of (S)-cyano-3-phenoxy-benzyl (1R, cis)-2,2-dimethyl-3-[(Z)-3-oxo-3-(1,1,1,3,3,3-hexafluoro-isopropoxy)-1-propenyl]-cyclopropane carboxylate to 500 parts of prochloraze.

EXAMPLE 7

A spray was prepared containing one part of pentafluorobenzyl (1R,cis)(E)-2,2-dimethyl-3-(3-oxo-3-methoxy-2-fluoro-1-propenyl)-cyclopropane carboxylate to 50 parts of flusilazol per liter.

EXAMPLE 8

An acetonic solution was prepared containing 100 mg of tefluthrin and 50 g of diclobutrazole per liter of acetone.

EXAMPLE 9

An acetonic solution was prepared containing 100 mg of tefluthrin and 50 g of triadimenol per liter of acetone.

EXAMPLE 10

An acetonic solution was prepared containing 100 mg of tefluthrin and 50 mg of imazalil per liter of acetone.

EXAMPLE 11

An acetonic solution was prepared containing 100 mg of tefluthrin and 50 mg of propiconazole per liter of acetone.

EXAMPLE 12

An acetonic solution was prepared containing 100 mg of tefluthrin and 50 mg of fenpropymorph per liter of acetone.

BIOLOGICAL RESULTS

1) Study of the synergy of activities on Diabrotica of compositions containing 1 part of tefluthrin to 500 parts of prochloraze.

The test insects were last stage larvae of Diabrotica treated by topical application of a 1 $\mu$l acetonic solution using an Arnold micromanipulator. 10 larvae per dose were used and the mortality check was carried out 24 hours after treatment. The mixture of 500 parts of prochloraze to 1 part of tefluthrin increased the insecticidal activity of the tefluthrin on Diabrotica by approximately four times.

2) Study of the synergy of activities on Diabrotica of compositions containing 1 part of tefluthrin to 50 parts of prochloraze or of flusilazol or of imazalil or of propiconazole.

The method was the same as that described previously.

a) The mixture of 50 parts of prochloraze and of one part of tefluthrin increased the insecticidal activity of the tefluthrin on Diabrotica by approximately twice.

b) The mixture of 50 parts of flusilazol and of one part of tefluthrin increased the insecticidal activity of the tefluthrin on Diabrotica by approximately 5.3 times.

c) The mixture of 50 parts of imazalil and of one part of tefluthrin increased the insecticidal activity of the tefluthrin on Diabrotica by approximately four times.

d) The mixture of 50 parts of propiconazole and of one part of tefluthrin iceased the insecticidal activity of the tefluthrin on Diabrotica by approximately four times.

3) Study of the synergy of activities on the household fly of compositions containing 1 part of deltamethrin per 500 parts of prochloraze.

The test insects were female household flies 4 to 5 days old, and they were treated by topical application of a 1 μl acetonic solution using on Arnold micromanipulator. 30 insects were used per dose and the mortality check was carried out 24 hours after treatment. The mixture of 500 parts of prochloraze to 1 part of deltamethrin increased the insecticidal activity of the deltamethrin on the household fly in a considerable fashion.

4) Study of the synergy of activities on Lepidoptera (*Spodoptera littoralis*) of compositions containing 1 part of deltamethrin to 500 parts of prochloraze or flusilazol.

The test insects were the third stage larvae of *Spodoptera littoralis* treated by topical application of a 1 μl acetonic solution using an Arnold micromanipulator and 20 larvae were used per dose. The mortality check was carried out 48 hours after treatment.

a) The mixture of 500 parts of prochloraze to 1 part of deltamethrin increased the insecticidal activity of the deltamethrin on *Spodoptera littoralis* by approximately 2.4 times.

b) The mixture of 500 parts of flusilazol to 1 part of deltamethrin increased the insecticidal activity of the deltamethrin on *Spodoptera littoralis* by approximately 2.6 times.

5) Study of the synergy of activities on lepidoptera (*Spodoptera littoralis*) of compositions containing 1 part of deltamethrin to 50 parts of prochloraze or of flusilazol. The method was the same as that described previously.

a) The mixture of 50 parts of prochloraze to 1 part of deltamethrin increased the insecticidal activity of the deltamethrin on *Spodoptera littoralis* by approximately 1.3 times.

b) The mixture of 50 parts of flusilazol to 1 part of deltamethrin increased the insecticidal activity of the deltamethrin on *Spodoptera littoralis* by approximately 1.8 times.

6) Study of the syngergy of activities on acaridae of compositions containing 1 part of (S)-cyano-3-phenoxybenzyl (1R,cis) 2,2-dimethyl-3-[(Z)-3-oxo-3-(1,1,1,3,3,3-hexafluoro-isopropoxy)-1-propenyl]-cyclopropane carboxylate (compound A) to 500 parts of prochloraze.

The test acaridae were one week old females placed on haricot bean leaves treated beforehand with a 2 ml solution of half water-half acetone using a FISHER gun and 30 acaridae were used per dose. The efficiency check took place 3 days after infestation and the mixture of 500 parts of prochloraze with one part of product A increased the acaricidal activity of product A on *Tetranychus urticae* by approximately 4.7 times.

7) Study of the synergy of activities on acaridae of compositions containing 1 part of product A per 50 parts of prochloraze.

The method was the same as that described previously. The mixture of 50 parts of prochloraze with 1 part of product A increased the acaricidal activity of product A on *Tetranychus urticae* by approximately 1.9 times.

8) Study of the synergy of activities on Diabrotica of compositions containing 1 part of tefluthrin per 50 parts of diclobutrazole or of triadimenol or of fenpropimorph.

The mixture of 50 parts of diclobutrazole, of triadimenol or of fenpropimorph notably increased the activity of the tefluthrin.

9) By adding piperonyl butoxide to the preceding compositions, the insecticidal activity was increased considerably.

Various modifications of the compositions and method of the invention may be made without departing from the spirit or scope thereof and it is to be understood that the invention intended to be limited only as defined in the appended claims.

What we claim is:

1. A synergistic insecticidal composition comprising a synergistic mixture of 10 to 1,000 parts by weight of prochloraze and 1 part by weight of tefluthrin.

2. A composition of claim 1 containing 30 to 600 parts by weight of prochloraze.

3. A composition of claim 1 containing 40 to 60 parts by weight of prochloraze.

4. A method of combatting insects comprising contacting the insects with an insecticidally effective amount of a synergistic insecticidal composition of claim 1.

5. A method of claim 4 containing 30 to 600 parts by weight of prochloraze.

6. A method of claim 4 containing 40 to 60 parts by weight of prochloraze.

* * * * *